（12）United States Patent
Katsurada et al.

(10) Patent No.: US 9,913,966 B2
(45) Date of Patent: Mar. 13, 2018

(54) BALLOON CATHETER

(71) Applicant: ASAHI INTECC CO., LTD., Nagoya-shi, Aichi (JP)

(72) Inventors: Takeharu Katsurada, Nagoya (JP); Takeshi Mogi, Owariasahi (JP)

(73) Assignee: ASAHI INTECC CO., LTD., Nagoya-shi (JP)

( * ) Notice: Subject to any disclaimer, the term of this patent is extended or adjusted under 35 U.S.C. 154(b) by 156 days.

(21) Appl. No.: 14/944,449

(22) Filed: Nov. 18, 2015

(65) Prior Publication Data

US 2016/0263355 A1 Sep. 15, 2016

(30) Foreign Application Priority Data

Mar. 10, 2015 (JP) ................. 2015-047146

(51) Int. Cl.
*A61M 25/10* (2013.01)
*A61M 25/01* (2006.01)
(Continued)

(52) U.S. Cl.
CPC ......... *A61M 25/1002* (2013.01); *A61B 17/22* (2013.01); *A61M 25/0147* (2013.01);
(Continued)

(58) Field of Classification Search
CPC ................ A61M 2025/0063; A61M 25/1006
See application file for complete search history.

(56) References Cited

U.S. PATENT DOCUMENTS 4,362,163 A * 12/1982 Krick ................ A61M 25/0102
604/526
4,586,923 A * 5/1986 Gould ............... A61M 25/0147
600/434
(Continued)

FOREIGN PATENT DOCUMENTS

CA 2468108 A1 6/2003
EP 0 578 777 B1 1/1998
(Continued)

OTHER PUBLICATIONS

Aug. 2, 2016 Extended European Seach Report issued in European Application No. 16153560.4.
(Continued)

*Primary Examiner* — Alexander Orkin
(74) *Attorney, Agent, or Firm* — Oliff PLC

(57) ABSTRACT

A balloon catheter comprises a balloon, an outer tube connected to a proximal end of the balloon, an inner tube disposed inside the outer tube and having a distal end attached to a distal end of the balloon, a protruded-depressed portion formed on an outer periphery of the inner tube, and a core wire disposed between the outer tube and the inner tube. The core wire has a bulged portion sandwiched between the outer tube and a depressed portion of the protruded-depressed portion. The balloon catheter can transmit a force from the core wire to both the outer tube and the inner tube regardless of whether the force is generated by pushing or pulling a proximal end portion of the balloon catheter. Additionally, the core wire can move appropriately to maintain the flexibility of the balloon catheter even when the balloon catheter bends.

8 Claims, 8 Drawing Sheets

(51) Int. Cl.
*A61B 17/22* (2006.01)
*A61M 25/00* (2006.01)
(52) U.S. Cl.
CPC ...... *A61M 25/104* (2013.01); *A61M 25/1006* (2013.01); *A61B 2017/22062* (2013.01); *A61M 2025/0063* (2013.01); *A61M 2025/015* (2013.01)

(56) References Cited

U.S. PATENT DOCUMENTS

| | | | | |
|---|---|---|---|---|
| 5,147,315 A | * | 9/1992 | Weber | A61B 17/43 600/35 |
| 5,176,637 A | * | 1/1993 | Sagae | A61M 25/104 604/103.09 |
| 5,242,396 A | * | 9/1993 | Evard | A61M 25/104 604/103.09 |
| 5,312,340 A | | 5/1994 | Keith | |
| 5,336,178 A | * | 8/1994 | Kaplan | A61B 8/12 604/103.01 |
| 5,417,658 A | | 5/1995 | Loney et al. | |
| 5,487,757 A | | 1/1996 | Truckai et al. | |
| 5,514,093 A | | 5/1996 | Ellis et al. | |
| 5,545,133 A | | 8/1996 | Burns et al. | |
| 5,649,908 A | * | 7/1997 | Itoh | A61M 25/1006 604/103 |
| 5,690,613 A | | 11/1997 | Verbeek | |
| 6,436,090 B1 | | 8/2002 | Sanchez et al. | |
| 6,482,221 B1 | | 11/2002 | Hebert et al. | |
| 6,702,781 B1 | | 3/2004 | Reifart et al. | |
| 6,733,473 B1 | | 5/2004 | Reifart et al. | |
| 7,815,627 B2 | * | 10/2010 | Von Oepen | A61M 25/10 604/525 |
| 8,088,121 B2 | | 1/2012 | Nishide et al. | |
| 8,403,885 B2 | | 3/2013 | Arana et al. | |
| 2002/0142119 A1 | * | 10/2002 | Seward | A61L 29/126 428/36.9 |
| 2004/0006305 A1 | * | 1/2004 | Hebert | A61M 25/0021 604/96.01 |
| 2004/0019324 A1 | * | 1/2004 | Duchamp | A61M 25/005 604/103.09 |
| 2012/0226231 A1 | | 9/2012 | Nishigishi | |
| 2012/0253447 A1 | | 10/2012 | Hayasaka et al. | |
| 2012/0296367 A1 | | 11/2012 | Grovender et al. | |
| 2016/0317789 A1 | * | 11/2016 | Segi | A61M 25/1006 |

FOREIGN PATENT DOCUMENTS

| | | |
|---|---|---|
| EP | 1 787 673 A1 | 5/2007 |
| EP | 1787673 A1 | 5/2007 |
| EP | 2 389 973 A1 | 11/2011 |
| EP | 2 495 006 A1 | 9/2012 |
| EP | 2859908 A1 | 4/2015 |
| JP | 2012-020077 A | 2/2012 |
| JP | 2012-183127 A | 9/2012 |
| JP | 2013106798 A | 6/2013 |
| WO | 92/17236 A1 | 10/1992 |
| WO | 2014/141440 A1 | 9/2014 |

OTHER PUBLICATIONS

May 11, 2017 Search Report issued in European Patent Application No. 17151391.4.
Sep. 30, 2016 Search Report issued in European Patent Application No. 16155233.6.
Jul. 26, 2017 Office Action issued in U.S. Appl. No. 14/978,345.
Jan. 11, 2018 Office Action issued in Japanese Patent Application No. 2015-047146.

* cited by examiner

BALLOON CATHETER

CROSS REFERENCE TO RELATED APPLICATION

This application claims priority to Japanese Application No. 2015-047146 filed on Mar. 10, 2015, the content of which is incorporated by reference herein in its entirety.

BACKGROUND

The disclosed embodiments relate to a medical device. Specifically, the disclosed embodiments relate to a balloon catheter.

Balloon catheters, which are used for expanding a stenosis site and the like in a lumen such as a blood vessel, are traditionally known.

A balloon catheter mainly comprises a balloon as an expanding object, an outer tube attached to a proximal end portion of the balloon, and an inner tube disposed inside an inner cavity of the outer tube and having a distal end portion attached to a distal end portion of the balloon.

The outer tube is designed for allowing an expansion liquid such as physiological saline to flow through a cavity defined between the outer tube and the inner tube in order to expand the balloon. The inner tube is designed so that a guide wire may be inserted into the inner tube in order to guide the balloon catheter to an affected area.

In general, a balloon catheter is used as follows: an operator such as a physician holds the balloon catheter at a proximal end portion of the balloon catheter and pushes a distal end portion of the balloon catheter into a blood vessel. Therefore, in order to position the balloon in a desired location of an affected area, excellent pushability into the affected area and excellent maneuverability of the distal portion are required.

Japanese Patent Application Laid-Open No. 2012-20077 describes a balloon catheter comprising a core wire inserted between a catheter shaft (an outer tube) and an inner shaft (an inner tube) in addition to the configuration described above, wherein the core wire is sandwiched between the outer tube and the inner tube.

According to Japanese Patent Application Laid-Open No. 2012-20077, the balloon catheter can supposedly improve the pushability of the balloon catheter without the need for a complicated process by simply sandwiching the core wire between the outer tube and the inner tube.

However, the balloon catheter described in Japanese Patent Application Laid-Open No. 2012-20077 has the following problems. Although the pushability of the catheter may be improved, in a case where the proximal end portion of the balloon catheter is pulled, the resulting pulling force cannot be transmitted to the balloon catheter through the core wire. Further, in a case where a pushing force against the proximal end portion of the balloon catheter is very strong, the core wire will move between the outer tube and the inner tube in the distal direction. Therefore, the core wire will be fixed between the outer tube and the inner tube, interfering with the flexibility of the balloon catheter.

SUMMARY

The disclosed embodiments address the above problems. An objective of the disclosed embodiments is to provide a balloon catheter in which a function for transmitting a force from a core wire to both an outer tube and an inner tube can be maintained regardless of whether the force is generated by pushing or pulling the proximal end portion of the balloon catheter, and in which the core wire is allowed to move appropriately to maintain the flexibility of the balloon catheter even when the balloon catheter bends.

In order to address the aforementioned problems, the disclosed embodiments include a balloon catheter comprising a balloon, an outer tube connected to a proximal end of the balloon, an inner tube disposed inside the outer tube and having a distal end connected to a distal end of the balloon, a protruded-depressed portion (i.e., a convex-concave textured portion) formed on an outer periphery of the inner tube, and a core wire disposed between the outer tube and the inner tube. The core wire has a bulged portion (i.e., an enlarged portion) sandwiched between the outer tube and a depressed portion of the protruded-depressed portion. Therefore, a force can be transmitted from the core wire to both the outer tube and the inner tube regardless of whether the force is generated by pushing or pulling the proximal end portion of the balloon catheter. Additionally, the bulged portion of the core wire can move appropriately between depressed portions of the protruded-depressed portion to maintain the flexibility of the balloon catheter even when the balloon catheter bends.

The protruded-depressed portion may be formed by winding a wire around the outer periphery of the inner tube to form a coil body having a large pitch (that is, a coil body in which adjacent windings of the wire are spaced apart from each other when the balloon catheter is in an unbent state). Therefore, this simple configuration can allow the force of pushing and/or pulling to be transmitted from the core wire to both the outer tube and the inner tube, and a kink in the inner tube can be prevented in addition to the advantageous effects described above.

A surface of the coil body may be coated with a resin so that the outer periphery of the inner tube forms streamlined (smoothed) protrusions and depressions along the shape of the wire of the coil body. Therefore, the bulged portion can move more smoothly in addition to the advantageous effects described above.

The balloon catheter of the disclosed embodiments may satisfy the relationship $Dc > Da > Db$, wherein $Da$ represents a distance between an inner wall of the outer tube and a base of each of the depressed portions of the protruded-depressed portion in a radial direction of the balloon catheter, $Db$ represents a distance between the inner wall of the outer tube and an apex of each of the protruded portions of the protruded-depressed portion in the radial direction of the balloon catheter, and $Dc$ represents an outer diameter of the bulged portion. Therefore, when the proximal end portion of the balloon catheter is pushed and/or pulled, the resulting force can be better transmitted from the core wire to both the outer tube and the inner tube in addition to the advantageous effects described above.

DETAILED DESCRIPTION OF EMBODIMENTS

The configuration of a balloon catheter according to the disclosed embodiments will be described below with reference to the Figures. In each of FIGS. 1 to 8, the left side corresponds to a distal side (a front side) that is to be inserted into the body, and the right side corresponds to a proximal side (a base side) that is to be operated by an operator such as a physician. For parts in common with each configuration, description will be omitted and the same reference numbers will be assigned in the figures.

Figure 1:
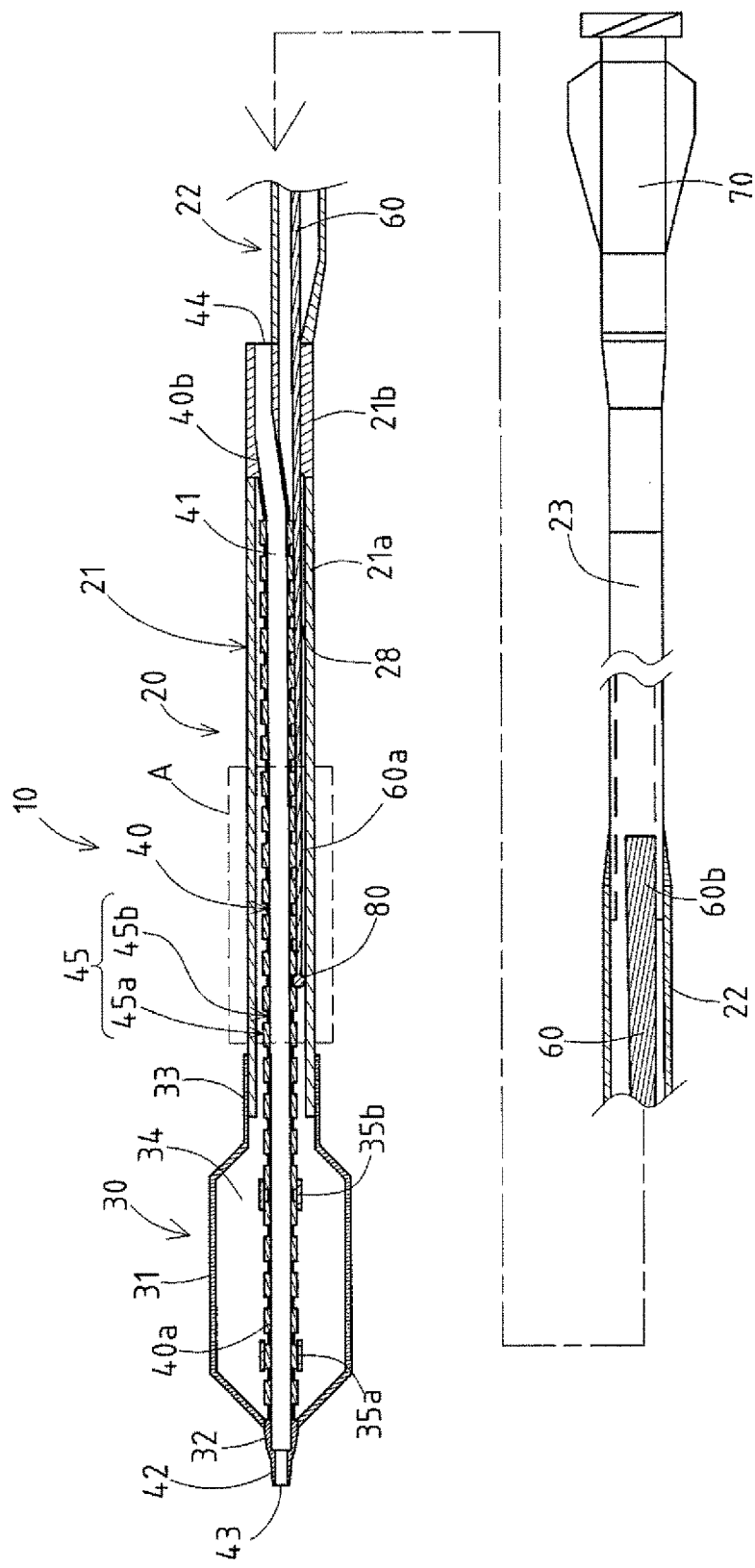
FIG. 1 shows a schematic overall view of a balloon catheter according to the disclosed embodiments.
Figure 2:
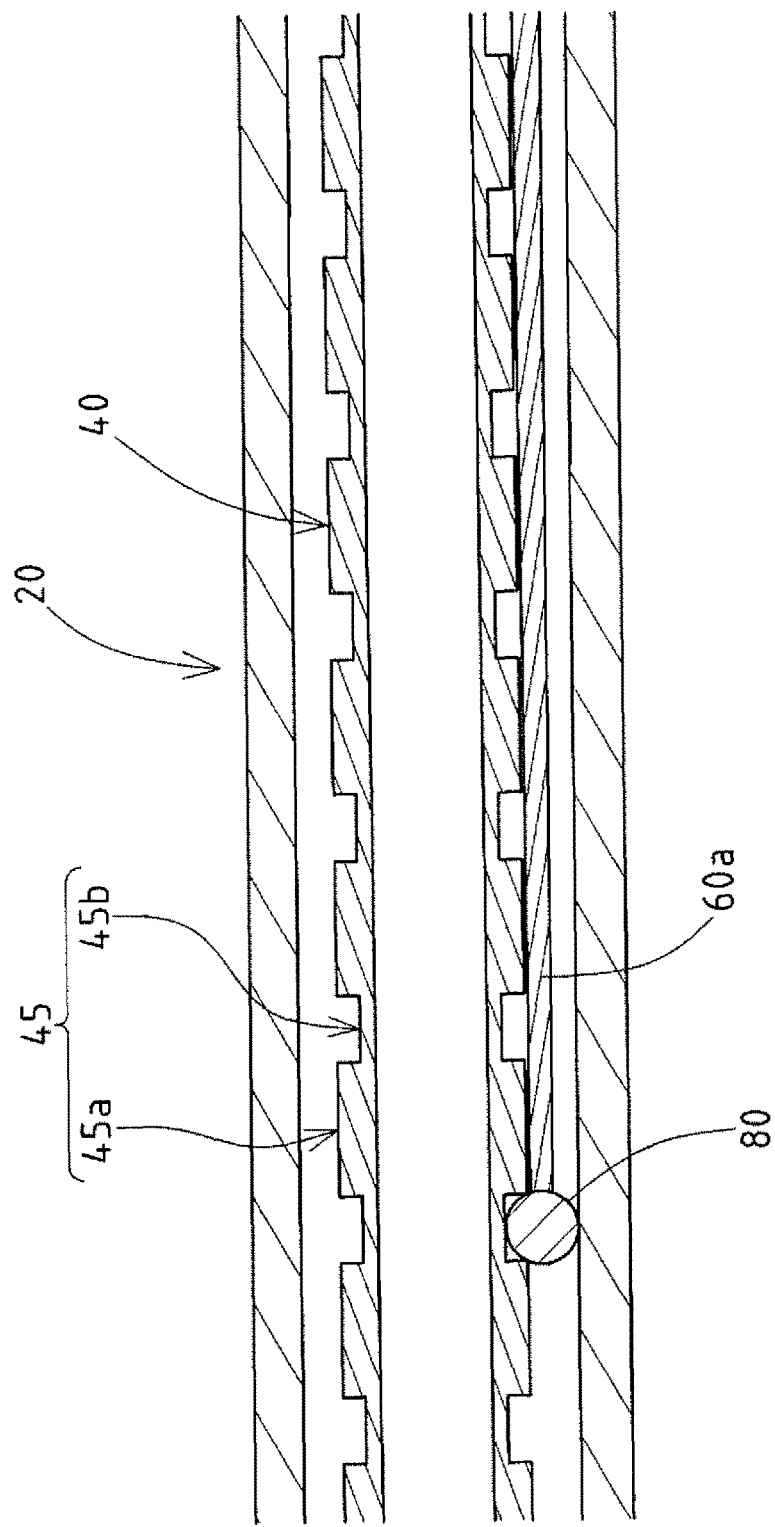
FIG. 2 shows a partial enlarged view of region A of FIG. 1.

FIG. 1 shows a schematic overall view of a balloon catheter according to the disclosed embodiments, and FIG. 2 shows a partial enlarged view of region A of FIG. 1.

A balloon catheter 10 shown in FIG. 1 comprises a balloon 30, an outer tube 20 connected to a proximal end portion of the balloon 30, an inner tube 40 inserted inside the outer tube 20 and having a distal end connected to a distal end of the balloon 30, a hypotube 23 connected to a proximal end of the outer tube 20, a core wire 60 inserted between the outer tube 20 and the inner tube 40 and having a proximal end connected to a distal end portion of the hypotube 23, and a connector 70 connected to a proximal end portion of the hypotube 23.

The balloon 30 comprises an expanding part 31 that expands due to the pressure of a liquid injected inside, a distal attachment part 32 connected to the distal end of a distal end portion 40a of the inner tube 40, and a proximal attachment part 33 connected to an outer periphery of a distal end of the outer tube 20. The expanding part 31 can be expanded with the pressure of the liquid injected inside to form an inner cavity 34 and to have a bag-like shape. Further, the inner cavity 34 of the balloon 30 communicates with an inner lumen 28 of the outer tube 20.

The outer tube 20 is a tubular body having a distal end outer tube 21 located on a distal side of the outer tube 20 and a proximal end outer tube 22 located on a proximal side of the outer tube 20. The inner lumen 28 extends continuously from the distal end outer tube 21 to the proximal end outer tube 22. Further, a liquid for expanding the balloon 30 can flow through the inner lumen 28 of the outer tube 20.

The distal end outer tube 21 and the proximal end outer tube 22 may be formed from a resin such as polyamide, polyamide elastomer, polyolefin, polyester, or polyester elastomer, for example.

The distal end outer tube 21 comprises a body tube 21a located on a distal side of the distal end outer tube 21, and a port tube 21b located on a proximal side of the distal end outer tube 21. The proximal attachment part 33 of the balloon 30 is connected to an outer periphery of a distal end of the body tube 21a.

The port tube 21b has an inner cavity in communication with the inner lumen 28 and an opening (a proximal end opening) 44 in which a proximal end portion 40b of the inner tube 40 described below is open to the environment. Note that the port tube 21b may be formed from a resin harder than that of the body tube 21a.

The inner tube 40 is a tubular body having a distal end portion 40a and the proximal end portion 40b and is inserted coaxially with the outer tube 20 into the inner lumen 28 of the distal end outer tube 21 of the outer tube 20. The inner tube 40 has an inner lumen 41 in which a guide wire not shown in the figure may be inserted.

Further, a protruded-depressed portion 45 comprising protruded portions 45a and depressed portions 45b, which are of spiral or annular shapes in a longitudinal direction of the balloon catheter 10, is formed on an outer periphery of the inner tube 40 throughout the entire length of the inner tube 40. Note that the inner tube 40 may be formed of the same resin as the distal end outer tube 21 and the proximal end outer tube 22.

The distal end portion 40a of the inner tube 40 protrudes from a distal end of the distal end outer tube 21, and a tip 42 formed of a soft resin may be attached to a distal end of the distal end portion 40a.

The hypotube 23 is a metal tubular body. The proximal end outer tube 22 is connected to an outer periphery of the distal end portion of the hypotube 23, and the connector 70 is attached to the proximal end portion of the hypotube 23. Further, a proximal end portion 60b of the core wire 60 described below is connected to an inside of the distal end portion of the hypotube 23.

As a material of the hypotube 23, for example, a superelastic alloy such as stainless steel or a Ni—Ti alloy may be used.

The core wire 60 comprises a distal end portion 60a, the proximal end portion 60b, and a bulged portion 80 connected to a distal end of the distal end portion 60a and having a diameter larger than a wire diameter of the distal end portion 60a.

The proximal end portion 60b of the core wire 60 is connected to the inside of the distal end portion of the hypotube 23 by joining means such as welding, adhesives, and the like, and the bulged portion 80 disposed at the distal end portion 60a of the core wire 60 is sandwiched between the outer tube 20 and one of the depressed portions 45b of the protruded-depressed portion 45.

The connector 70 is a resin tubular member. When a liquid is supplied from an indeflator (not shown) attached to a proximal end of the connector 70, the liquid enters the inner cavity 34 of the balloon 30 from the hypotube 23 through the inner lumen 28 to expand the balloon 30.

The tip 42 is a tapered tubular member having an outer diameter that gradually decreases in the distal direction, and having a distal end opening 43 at a distal end of the tip 42. The tip 42 may be formed of a resin softer than that of the distal end portion 40a of the inner tube 40.

Further, two radiopaque markers 35a and 35b separated by a predetermined distance are attached to the distal end portion 40a of the inner tube 40 inside of the expanding part 31 of the balloon 30.

A case where the balloon catheter 10 is used in a procedure for expanding a stenosis site in the coronary artery of the heart will be described based on the above configuration.

A guide wire is inserted into the coronary artery of the heart having a stenosis site as a treatment target before operation of the balloon catheter 10 begins. First, an operator inserts a proximal end of this guide wire through the distal end opening 43 of the balloon catheter 10 and passes it through the inner lumen 41 of the inner tube 40, and then retrieves the guide wire through the proximal end opening 44. Subsequently, while holding the guide wire, a proximal end portion of the balloon catheter 10 is pushed in the distal direction to advance the balloon catheter 10 into the patient's blood vessel.

The pushing force with which an operator pushes is first transmitted to the outer tube 20 and the core wire 60 from the hypotube 23. In this case, the bulged portion 80 disposed at the distal end portion 60a of the core wire 60 is sandwiched between the outer tube 20 and one of the depressed portions 45b of the protruded-depressed portion 45, and thus the pushing force transmitted to the outer tube 20 and the core wire 60 is also transmitted to the inner tube 40.

Further, since the bulged portion 80 is sandwiched, but not fixed, between the outer tube 20 and one of the depressed portions 45b of the protruded-depressed portion 45, the bulged portion 80 is capable of moving in both the distal and proximal directions as needed. For example, the bulged portion 80 can move to a distally adjacent one of the depressed portions 45b in a case where the balloon catheter 10 bends toward the side of the core wire 60 due to the serpentine state of a patient's blood vessel. On the other hand, in a case where the balloon catheter 10 bends toward the opposite side of the core wire 60, the bulged portion 80 can move to a proximally adjacent one of the depressed portions 45b. Therefore, the flexibility of the balloon catheter 10 can be maintained.

If the bulged portion 80 was both sandwiched and fixed (that is, adhered) between the outer tube 20 and one of the depressed portions 45b of the protruded-depressed portion 45, the balloon catheter 10 would be difficult to bend due to the rigidity of the core wire 60 and the like in a case where the balloon catheter 10 bends toward the side of the core wire 60 or the opposite side of the core wire 60 depending on the serpentine state of a patient's blood vessel. In contrast, the balloon catheter 10 in which the bulged portion 80 is not fixed in place will bend flexibly depending on the serpentine state of a patient's blood vessel since the rigidity of the core wire 60 will not interfere with the maneuverability of the balloon catheter 10 through a curved vessel.

Further, the bulged portion 80 moves to the distally adjacent one of the depressed portions 45b when the pushing force to the core wire 60 exceeds a predetermined value, and thus an excessive force will not be transmitted to a distal end of the balloon catheter 10. An operator can therefore safely operate the balloon catheter 10.

Subsequently, an operator positions the balloon 30 at a stenosis site as a target site while observing markers 35a and 35b under radioscopy, and then supplies a liquid from an indeflator (not shown) connected to the connector 70. At this time, the liquid flows into the inner lumen 28 of the outer tube 20, and flows out from the distal end of the distal end outer tube 21 into the inner cavity 34 of the balloon 30 to expand the balloon 30, which in turn expands the stenosis site at the same time.

After expanding the stenosis site with the balloon 30, the operator discharges the liquid from the balloon 30 with the indeflator. That is, the liquid flows out of the inside of the balloon 30 and is discharged through the inner lumen 28 of the outer tube 20. Then, the balloon catheter 10 is pulled out of the patient's body to complete the procedure.

A pulling force is also first transmitted to the outer tube 20 and the core wire 60 from the hypotube 23 when the operator pulls the balloon catheter 10 out of the patient's body. In this case, the bulged portion 80 disposed at the distal end portion 60a of the core wire 60 is sandwiched between the outer tube 20 and one of the depressed portions 45b of the protruded-depressed portion 45, and thus the pulling force transmitted to the outer tube 20 and the core wire 60 is also transmitted to the inner tube 40, enabling smooth withdrawal of the balloon catheter 10 from the patient's body.

In the case of the balloon catheter 10, the following operational effects can be achieved.

(1) The balloon catheter 10 comprises the balloon 30, the outer tube 20 connected to the proximal end of the balloon 30, the inner tube 40 disposed inside the outer tube 20 and having a distal end connected to the distal end of the balloon 30, the protruded-depressed portion 45 formed on the outer periphery of the inner tube 40, and the core wire 60 disposed between the outer tube 20 and the inner tube 40. The core wire 60 has the bulged portion 80 sandwiched between the outer tube 20 and one of the depressed portions 45b of the protruded-depressed portion 45. Therefore, a force can be transmitted from the bulged portion 80 of the core wire 60 to both the outer tube 20 and the inner tube 40 regardless of whether the force is generated by pushing or pulling the proximal end portion of the balloon catheter 10.

(2) Even if the balloon catheter 10 bends, the bulged portion 80 of the core wire 60 can move appropriately between the depressed portions 45b of the protruded-depressed portion 45, and thus the flexibility of the balloon catheter 10 can be maintained.

Figure 3:
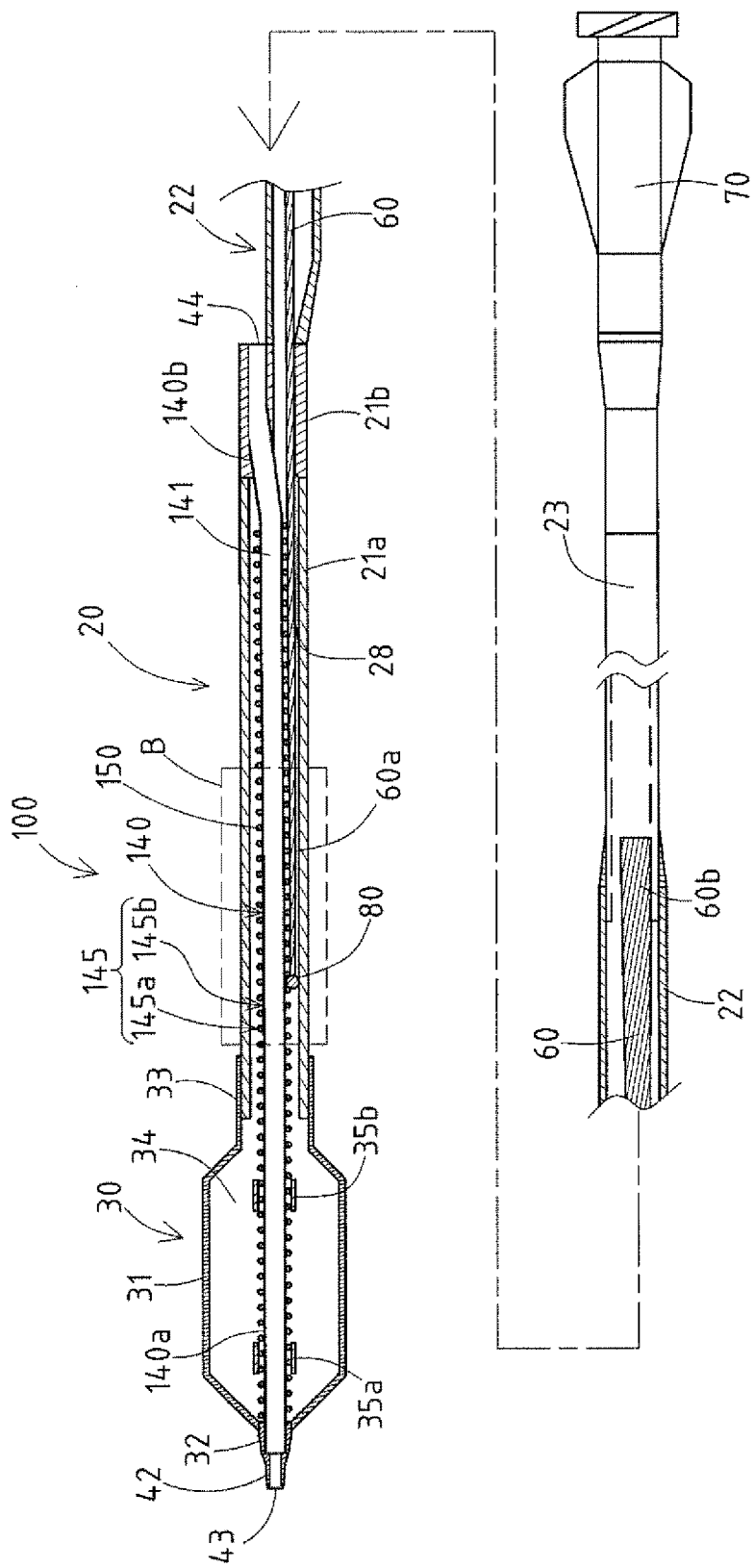
FIG. 3 shows a schematic overall view of a balloon catheter according to the disclosed embodiments.
Figure 4:
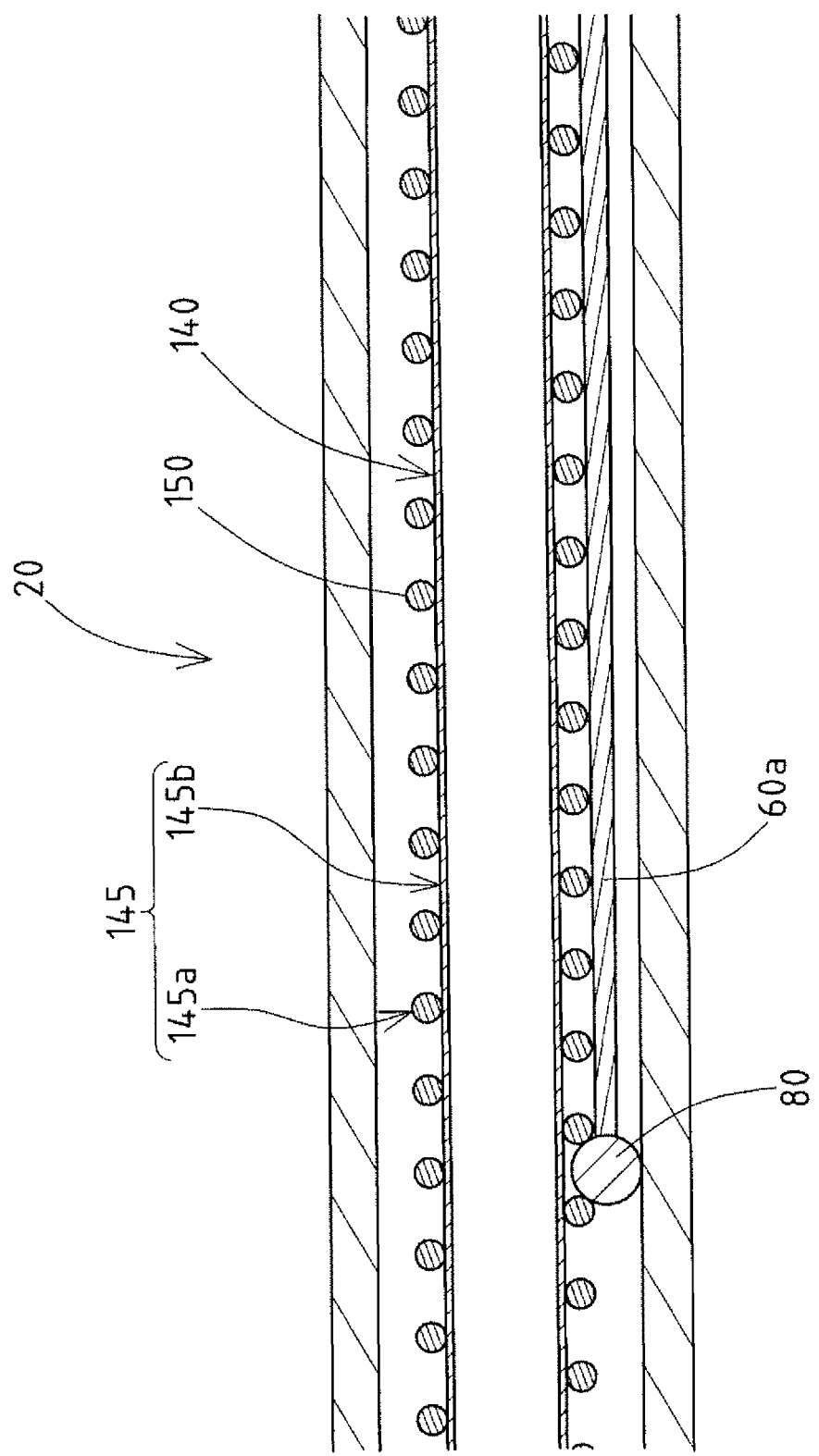
FIG. 4 shows a partial enlarged view of region B of FIG. 3.

FIG. 3 also shows a schematic overall view of a balloon catheter according to the disclosed embodiments. FIG. 4 shows a partial enlarged view of region B of FIG. 3.

A balloon catheter 100 shown in FIG. 3 has an inner tube different from that of the balloon catheter 10 described above. That is, an inner tube 140 of the balloon catheter 100 has a distal end portion 140a and a proximal end portion 140b, and is a tubular body which is inserted coaxially with the outer tube 20. In particular, the inner tube 140 is inserted into the inner lumen 28 of the distal end outer tube 21 of the outer tube 20. The inner tube 140 has an inner lumen 141 in which a guide wire not shown in the figure may be inserted.

Further, a protruded-depressed portion 145 comprising protruded portions 145a and depressed portions 145b is formed by spirally winding, in a longitudinal direction of the balloon catheter 100, a metal wire 150 with a circular cross section to form a coil body. The metal wire 150 is wound on an outer periphery of the inner tube 140 over the entire length of the inner tube 140. The metal wire 150 is wound with a large pitch such that adjacent windings of the metal wire 150 are spaced apart from each other when the balloon catheter 100 is in an unbent state.

As described above, the metal wire 150 with a circular cross section is spirally wound in the longitudinal direction of the balloon catheter 100 to form a coil body having a large pitch in order to form the protruded-depressed portion 145. However, a resin wire may instead be used to form the protruded-depressed portion 145, or a metal wire with a rectangular cross section or a resin wire with a rectangular cross section may instead be used to form the protruded-depressed portion 145. Further, two or more metal or resin wires with a circular or rectangular cross section may be used to form the protruded-depressed portion 145, or one twisted wire formed by twisting together two or more metal or resin wires with a circular cross section may be used to form the protruded-depressed portion 145. Further, two or more twisted wires formed by twisting together two or more metal or resin wires with a circular cross section may be used to form the protruded-depressed portion 145.

The bulged portion 80 disposed at the distal end portion 60a of the core wire 60 is sandwiched between the outer tube 20 and one of the depressed portions 145b of the protruded-depressed portion 145. In a case where the balloon catheter 100 as described above is used in a procedure for expanding a stenosis site in the coronary artery of the heart, a pushing and/or pulling force can be transmitted from the bulged portion 80 of the core wire 60 to both the outer tube 20 and the inner tube 140, and a kink in the inner tube 140 can be prevented by utilizing this simple configuration of the protruded-depressed portion 145 formed by winding the metal wire 150 around the outer periphery of the inner tube 140 to form a coil body having a large pitch.

Figure 5:
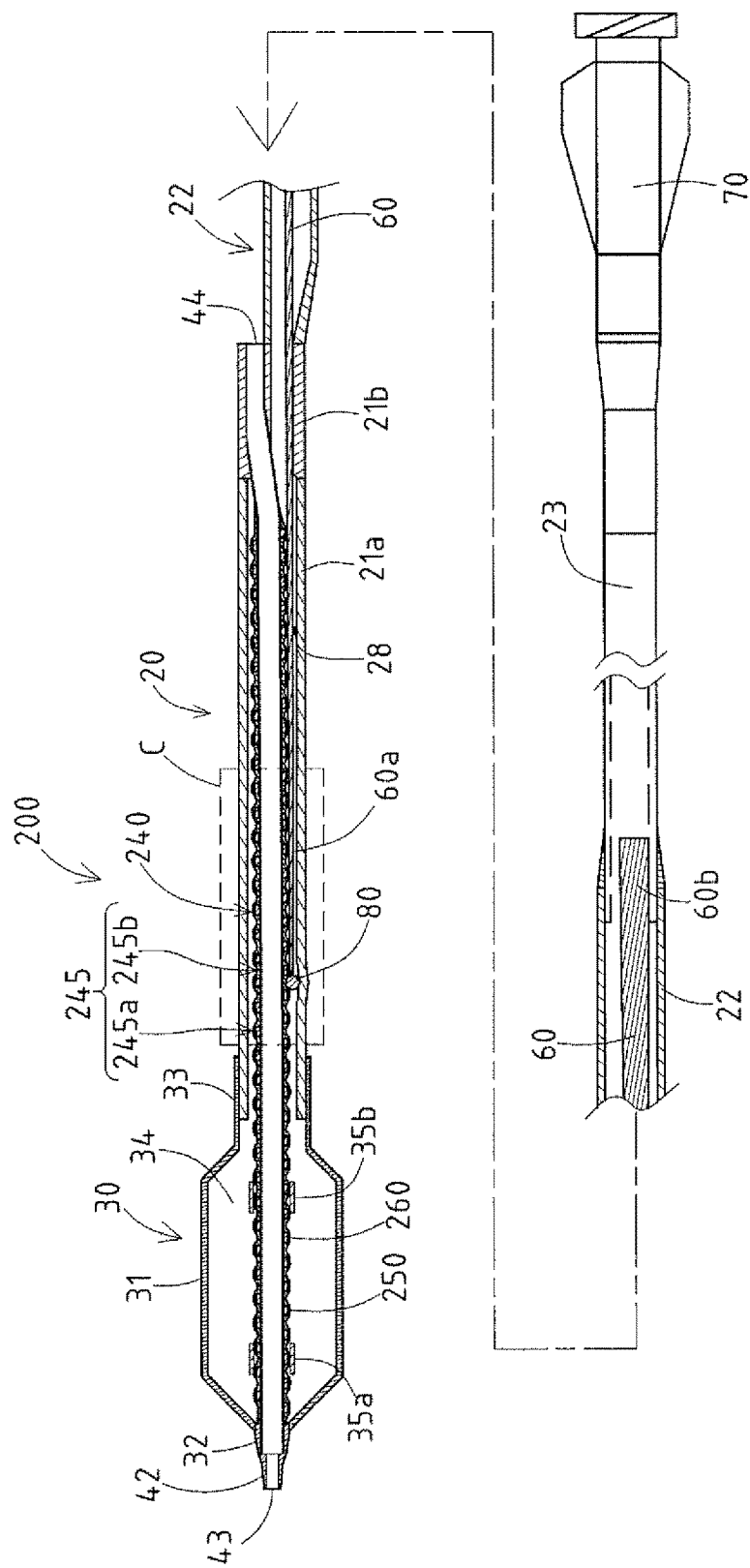
FIG. 5 shows a schematic overall view of a balloon catheter according to the disclosed embodiments.
Figure 6:
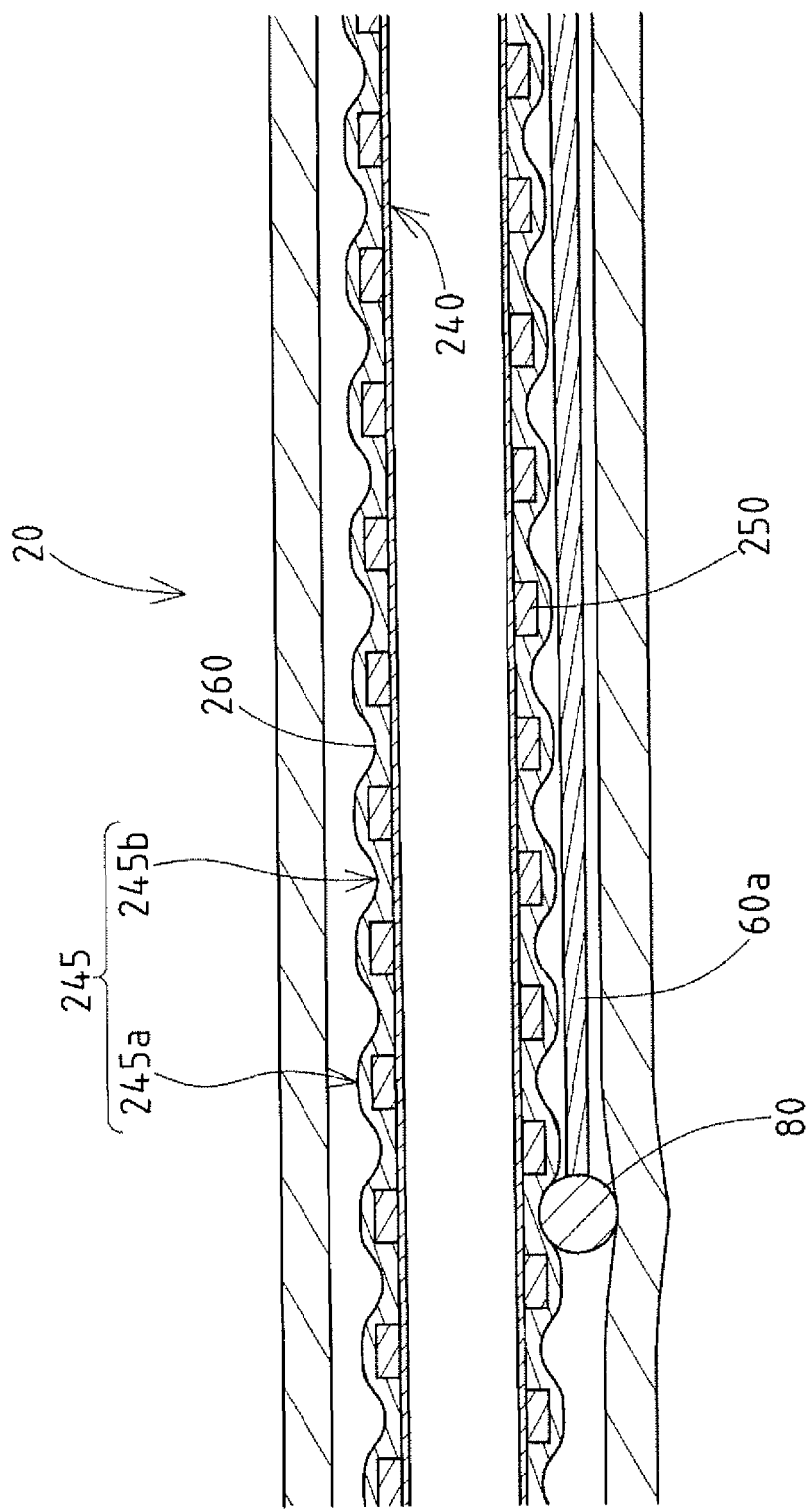
FIG. 6 shows a partial enlarged view of region C of FIG. 5.

FIG. 5 shows a schematic overall view of a balloon catheter according to the disclosed embodiments. FIG. 6 shows a partial enlarged view of region C of FIG. 5.

A balloon catheter 200 shown in FIG. 5 has an inner tube different from that of the balloon catheter 10 described above. That is, a metal wire 250 with a rectangular cross section is spirally wound in a longitudinal direction of the balloon catheter 200 on an outer periphery of an inner tube 240 to form a coil body with a large pitch that covers the entire length of the inner tube 240. A surface of the metal wire 250 is coated with a resin 260 to form streamlined protrusions and depressions on an outer periphery of the inner tube 240 along the shape of the metal wire 250 with a rectangular cross section. The protrusions and depressions form a protruded-depressed portion 245 comprising protruded portions 245a and depressed portions 245b. That is, the streamlined protrusions and depressions correspond to the protruded portions 245a and the depressed portions 245b, respectively, having smoothed surfaces.

As a resin material for forming the coating, a resin such as polyamide, polyamide elastomer, polyolefin, polyester, or polyester elastomer, for example, may be used.

As described above, the metal wire 250 with a rectangular cross section is spirally wound in the longitudinal direction of the balloon catheter 200 to form a coil body having a large pitch, thereby forming the protruded-depressed portion 245. However, a resin wire may instead be used to form the protruded-depressed portion 245, or a metal wire with a circular cross section or a resin wire with a circular cross section may instead be used to form the protruded-depressed portion 245. Further, two or more metal or resin wires with a circular or rectangular cross section may be used to form the protruded-depressed portion 245, or one twisted wire formed by twisting together two or more metal or resin wires with a circular cross section may be used to form the protruded-depressed portion 245. Further, two or more twisted wires formed by twisting together two or more metal or resin wires with a circular cross section may be used to form the protruded-depressed portion 245.

The bulged portion 80 disposed at the distal end portion 60a of the core wire 60 is sandwiched between the outer tube 20 and one of the depressed portions 245b of the protruded-depressed portion 245. In a case where the balloon catheter 200 is used in a procedure for expanding a stenosis site in the coronary artery of the heart, the bulged portion 80 can move smoothly, in addition to the advantageous effects described above, because the surface of the metal wire 250 of the coil body is coated with the resin 260 so that the outer periphery of the inner tube 240 forms streamlined protrusions and depressions along the shape of the metal wire with a rectangular cross section to form the protruded-depressed portion 245 comprising the protruded portions 245a and the depressed portions 245b.

Figure 7:
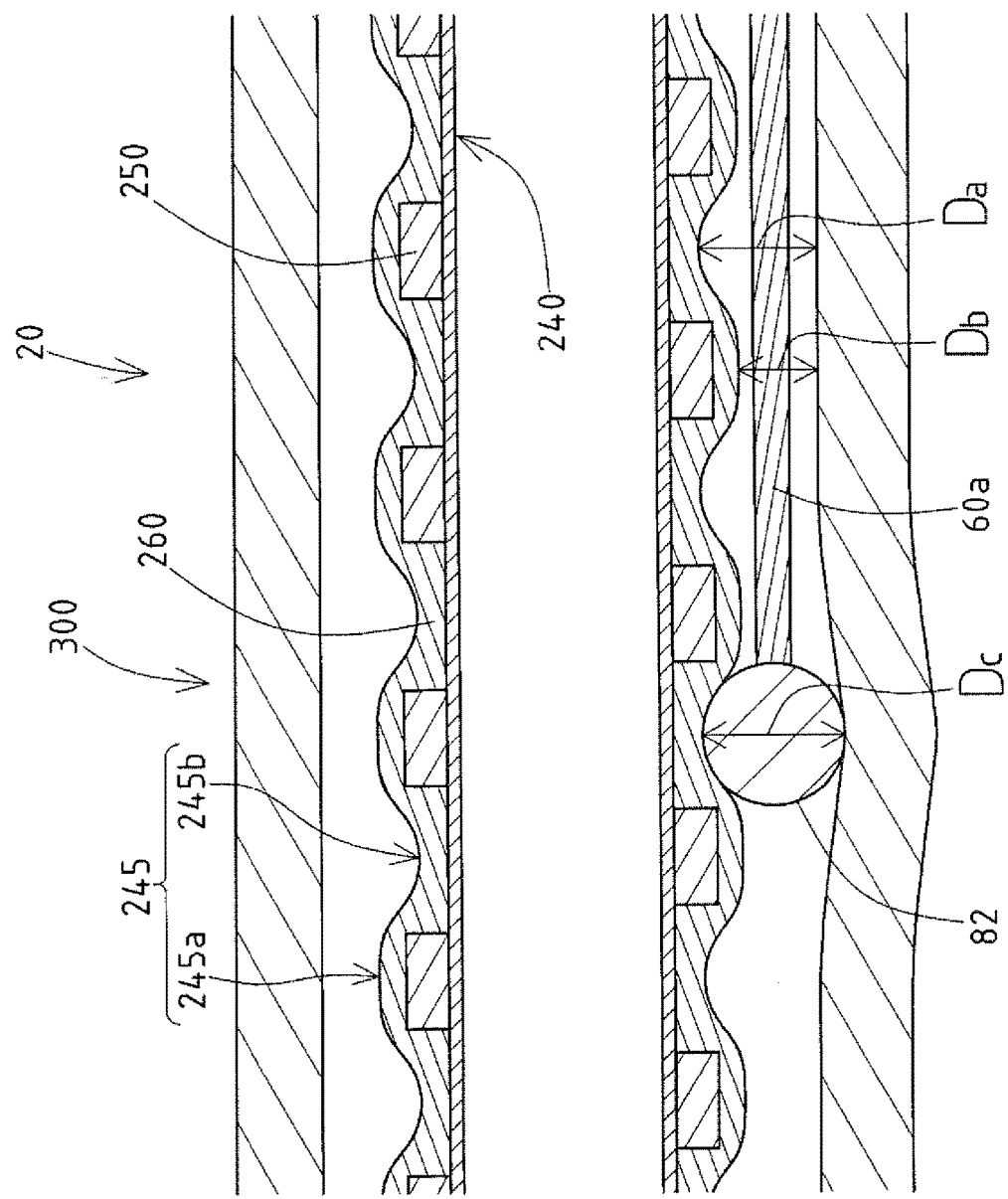
FIG. 7 shows an enlarged view of a main section of a balloon catheter according to the disclosed embodiments.
Figure 8:
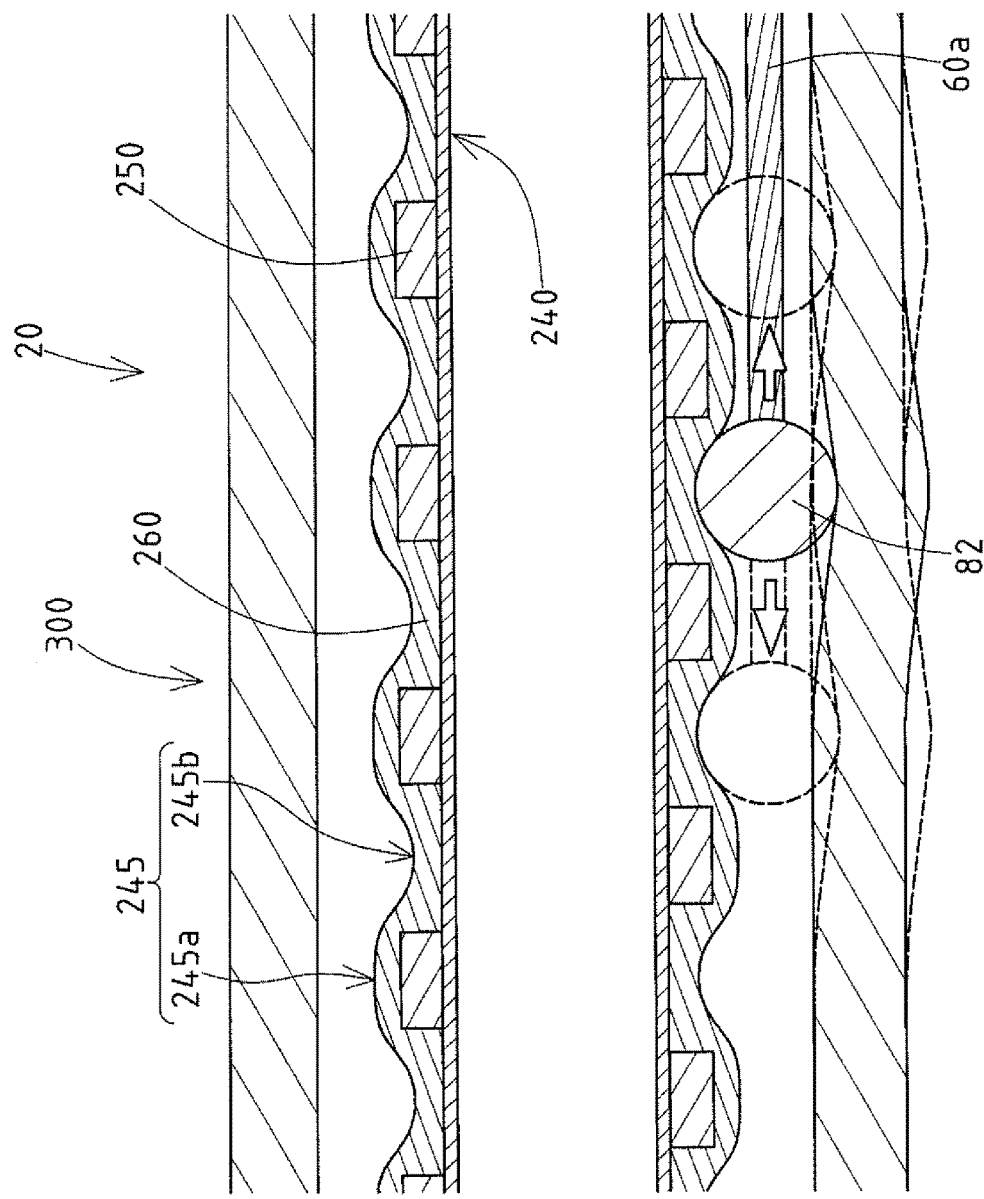
FIG. 8 shows a diagram illustrating movement of a bulged portion of a core wire of the balloon catheter of FIG. 7.

FIG. 7 shows an enlarged view of a main section of a balloon catheter 300 according to the disclosed embodiments. FIG. 8 shows a diagram illustrating the movement of a bulged portion 82. The balloon catheter 300 satisfies the relationship Dc>Da>Db, wherein Da represents a distance between an inner wall of the outer tube 20 and a base of each of the depressed portions 245b in a radial direction of the balloon catheter 300, Db represents a distance between the inner wall of the outer tube 20 and an apex of each of the protruded portions 245a in the radial direction of the balloon catheter 300, and Dc represents an outer diameter of the bulged portion 82. Therefore, the transferability of a pushing or pulling force from the core wire 60 to both the inner tube 240 and the outer tube 20 can be further improved.

Further, as shown in FIG. 8, when the balloon catheter 300 bends toward the side of the core wire 60 depending on the serpentine state of a patient's blood vessel, the bulged portion 82 can move to a distally adjacent one of the depressed portions 245b (toward the left side in the figure) to maintain the flexibility of the balloon catheter 300. On the other hand, when the balloon catheter 300 bends toward the opposite side of the core wire 60, the bulged portion 82 can move to a proximally adjacent one of the depressed portions 245b (toward the right side in the figure) to maintain the flexibility of the balloon catheter 300.

Note that although FIG. 8 describes the movement of the bulged portion 82 in the distal and proximal directions (toward the left and right sides of the figure, respectively), it is apparent that the bulged portion 80 described above can also move in a similar fashion.

Note that although the balloon catheters 10, 100, 200, 300 have been described in the context of use for the treatment of a blood vessel of the heart, they may be used in various procedures such as those for expanding a blood vessel of a lower limb or for expanding a dialysis shunt.

Further, the balloon catheters 10, 100, 200, 300 have the bulged portion 80, 82 provided at the distal end portion 60a of the core wire 60. However, the bulged portion 80, 82 may be provided at a middle portion of the core wire 60.

What is claimed is:

1. A balloon catheter comprising:
   a balloon;
   an outer tube connected to a proximal end of the balloon;
   an inner tube disposed inside the outer tube and having a distal end connected to a distal end of the balloon;
   a protruded-depressed portion formed on an outer periphery of the inner tube, the protruded-depressed portion including a plurality of protruded portions and a plurality of depressed portions along a longitudinal direction of the inner tube; and
   a core wire disposed between the outer tube and the inner tube,
   wherein:
   the core wire has a bulged portion sandwiched between the outer tube and a depressed portion of the plurality of depressed portions, and
   the bulged portion is configured to interact with the plurality of depressed portions to maintain flexibility of the balloon catheter when the balloon catheter is inserted into a patient's blood vessel.

2. The balloon catheter according to claim 1, wherein:
   the protruded-depressed portion is a wire wound around the outer periphery of the inner tube to form a coil body in which adjacent windings of the wire are spaced apart from each other when the balloon catheter is in an unbent state, and
   a surface of the coil body is coated with a resin so that a wave portion is formed by the plurality of protruded portions and the plurality of depressed portions.

3. The balloon catheter according to claim 2, satisfying Dc>Da>Db, wherein:
   Da represents a distance between an inner wall of the outer tube and a base of the depressed portion in a radial direction of the balloon catheter;

Db represents a distance between the inner wall of the outer tube and an apex of a protruded portion of the plurality of protruded portions in the radial direction of the balloon catheter, and Dc represents an outer diameter of the bulged portion.

4. The balloon catheter according to claim 2, wherein the bulged portion is provided at a distal end of the core wire.

5. The balloon catheter according to claim 2, wherein the bulged portion is freely movable relative to the outer tube and the depressed portion of the plurality of depressed portions.

6. The balloon catheter according to claim 1, satisfying Dc>Da>Db, wherein:

Da represents a distance between an inner wall of the outer tube and a base of the depressed portion in a radial direction of the balloon catheter;

Db represents a distance between the inner wall of the outer tube and an apex of a protruded portion of the plurality of protruded portions in the radial direction of the balloon catheter, and Dc represents an outer diameter of the bulged portion.

7. The balloon catheter according to claim 1, wherein the bulged portion is provided at a distal end of the core wire.

8. The balloon catheter according to claim 1, wherein the bulged portion is freely movable relative to the outer tube and the depressed portion of the plurality of depressed portions.

* * * * *